United States Patent [19]
Waldstreicher

[11] Patent Number: 5,942,519
[45] Date of Patent: Aug. 24, 1999

[54] PREVENTION OF PRECIPITATED ACUTE URINARY RETENTION

[75] Inventor: Joanne Waldstreicher, Scotch Plains, N.J.

[73] Assignee: Merck & Co., Inc., Rahway, N.J.

[21] Appl. No.: 09/178,138

[22] Filed: Oct. 23, 1998

Related U.S. Application Data

[60] Provisional application No. 60/065,953, Oct. 28, 1997.

[51] Int. Cl.$^6$ .................................................. A61K 31/47
[52] U.S. Cl. ............................................................ 514/284
[58] Field of Search .............................................. 514/284

[56] References Cited

U.S. PATENT DOCUMENTS

| | | | |
|---|---|---|---|
| 4,377,584 | 3/1983 | Rasmusson et al. | 424/258 |
| 4,760,071 | 7/1988 | Rasmusson et al. | 514/284 |
| 5,561,154 | 10/1996 | Bellamy et al. | 514/546 |
| 5,565,467 | 10/1996 | Batchelor et al. | 514/284 |
| 5,719,158 | 2/1998 | Durette et al. | 514/284 |

OTHER PUBLICATIONS

Barry et al., The Natural History of Patients with Benign Prostatic Hyperplasia as Diagonosed by North American Urologists. The J. of Uroloty, vol. 157, pp. 10–15 (1997).

MacConnell et al., The Effect of Finasteride on the Risk of Acute Urinary Retention and the Need for Surgical Treatment among Men with Benign Prostatic Hyperplasia, N. Eng. J. of Medicine, vol. 338(9), Feb. 1998, pp. 557–563 (some of this material was presented at the SIU 24th Congress, Montreal, Canada, Sep. 7–11, 1997.

Anderson et al., Finasteride Significantly Reduces Acute Urinary Retention and Need for Surgery in Patients with Symptomatic Benign Prostatic Hyperplasia, Urology, vol. 49, No. 6 (1997), pp. 839–845.

Jacobsen et al., Natural History of Prostatism: Risk Factors for Acute Urinary Retention. The J. of Urology, vol. 158, pp. 481–487 (1997).

Lieber, Proscar™ Long–Term Efficacy and Safety Studies (Pless) presented at Congress of the European Association of Urology, Mar. 21, 1998, Barcelona, Spain.

*Primary Examiner*—Raymond Henley, III
*Attorney, Agent, or Firm*—Catherine D. Fitch; Melvin Winokur

[57] ABSTRACT

This invention is concerned with the prevention of precipitated acute urinary retention in a subject male susceptible thereto by the administration of an inhibitor of 5α-reductase to the subject. The present invention also provides for a method of reducing the risk of precipitated acute urinary retention by the administration of a 5α-reductase inhibitor to the subject at risk therefor.

18 Claims, No Drawings

PREVENTION OF PRECIPITATED ACUTE URINARY RETENTION

CROSS-REFERENCE TO RELATED APPLICATIONS

The present application claims priority of U.S. provisional application Ser. No. 60/065,953, filed Oct. 28, 1997.

BACKGROUND OF THE INVENTION

Benign prostatic hyperplasia (BPH) is common in older men, with symptoms that impact quality of life, including interference with activities and perception of well being. BPH can be progressive, with risk of urinary retention, infections, bladder calculi and renal failure. Although many men with mild to moderate symptoms do well without intervention, bothersome symptoms and complications can progress in others, leading to medical therapy or surgery.

One of the complications of BPH is acute urinary retention, leading to catheterization. Acute urinary retention may be classified as either spontaneous or precipitated. Spontaneous acute urinary retention is often considered by patients to be the most serious outcome of BPH.

Spontaneous acute urinary retention is an episode of acute urinary retention that is due to BPH and is not tied to a precipitating event. The 5α-reductase inhibitor finasteride has been shown to be effective in treating BPH and in significantly reducing spontaneous acute urinary retention in patients with BPH. Andersen et al., *Urology*, 49(6), 839–845 (1997).

Precipitated acute urinary retention is an episode of acute urinary retention that is precipitated by at least one of the following factors: anesthesia or surgery within 72 hours; a precipitating medical event such as stroke or congestive heart failure; a medical condition such as prostatitis or urinary tract infection; or ingestion of medication or drugs known to precipitate retention, e.g., pseudoephedrine hydrochloride, cold medicine, pain medication such as narcotics or sedatives, or benadryl.

Until the present invention, nu medical therapy for BPH was known to decrease the risk of or prevent precipitated acute urinary retention.

The enzyme 5α-reductase catalyzes the reduction of testosterone (T) to the more potent androgen, 5α-dihydrotestosterone (dihydrotestosterone" or DHT), as shown below:

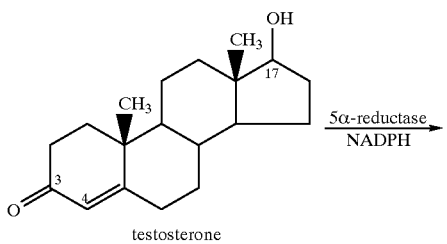

testosterone

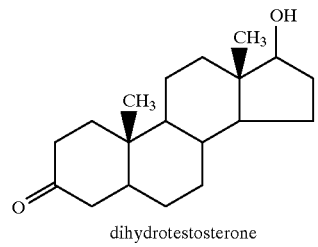

dihydrotestosterone

There are two isozymes of 5α-reductase in humans. One isozyme (type 1) predominates in the sebaceous glands of skin tissue. The other (type 2) predominates in the prostate.

Finasteride (17β-(N-tert-butylcarbamoyl)-3-oxo-4-aza-5α-androst-1-en-3-one), as shown below, is a potent inhibitor of the human type 2 enzyme.

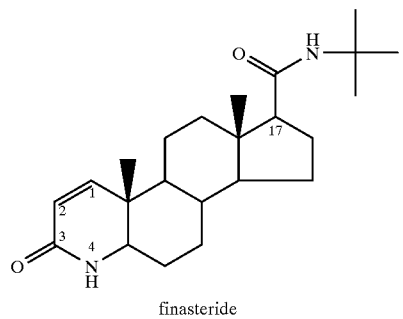

finasteride

Under the tradename PROSCAR®, finasteride is known to be useful in the treatment of hyperandrogenic conditions, see e.g., U.S. Pat. No. 4,760,071. Finasteride is currently prescribed for the treatment of benign prostatic hyperplasia (BPH), a condition affecting to some degree the majority of men over age 55.

Also known are compounds which are potent inhibitors of both 5α-reductase type 1 and type 2. These include the compound described in U.S. Pat. No. 5,565,467.

SUMMARY OF THE INVENTION

This invention is concerned with the prevention of precipitated acute urinary retention in a subject susceptible thereto by the administration of a compound which inhibits 5α-reductase to the subject. The present invention also provides for a method of reducing the risk of precipitated acute urinary retention by the administration of a compound which inhibits 5α-reductase to the subject at risk therefor.

DETAILED DESCRIPTION OF THE INVENTION

In one embodiment of the present invention is a method of preventing precipitated acute urinary retention in a subject susceptible thereto, comprising administration of an effective amount of an inhibitor of 5α-reductase to the subject.

In another embodiment of the present invention is provided a method for reducing the risk of precipitated acute urinary retention in a subject at risk therefor comprising administration of an effective amount of an inhibitor of 5α-reductase to the subject.

The present invention is further related to the use of a 5α-reductase inhibitor for the manufacture of a medicament useful in the prevention of or the reduction of the risk of precipitated acute urinary retention in a subject susceptible thereto.

Inhibitors of 5α-reductase type 2 are known in the art. For a given compound, its 5α-reductase type 2 inhibitory activity may be determined by assaying its activity as described in Example 3 in the present application. Compounds having an $IC_{50}$ under about 100 nM are 5α-reductase type 2 inhibitors useful in the present invention. Compounds also having both 5α-reductase type 2 and 5α-reductase type 1 activity, often called "dual inhibitors" are also compounds useful in the methods of the present invention. Further, inhibitors of 5α-reductase type 1 may be useful in the methods of the present invention.

Among the compounds useful in the methods of the present invention are those of structural formula I:

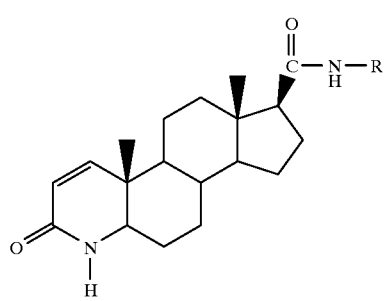

I wherein R is selected from:

(a) $C_{1-10}$ alkyl, unsubstituted or substituted with one to three halogen substituents, and (b) phenyl, unsubstituted or substituted with one to three substituents independently selected from halogen, methyl, and trifluoromethyl.

In one embodiment of compounds of structural formula I, R is selected from (a) unsubstituted $C_{1-10}$ alkyl, and (b) phenyl unsubstituted or substituted with one or two trifluoromethyl substituents.

In another embodiment of compounds of structural formula I, R is t-butyl.

In yet another embodiment of compounds of structural formula I, R is 2,5-bis(trifluoromethyl)phenyl.

Other inhibitors of 5α-reductase type 2 useful in the methods of the present invention include epristeride and turosteride, shown below:

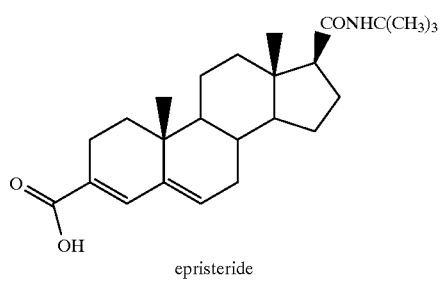

epristeride

-continued

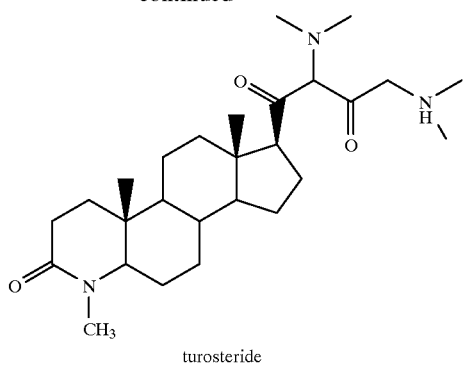

turosteride

The term "halo" or "halogen" is meant to include fluoro, chloro, bromo and iodo.

The term "$C_{1-10}$ alkyl" is meant to include both straight- and branched-chain alkyl groups of one to ten carbon atoms in length, not limited to: methyl, ethyl, propyl, butyl, pentyl, hexyl, heptyl, octyl, nonanyl, decyl and the isomers thereof such as isopropyl, isobutyl, secbutyl, t-butyl, isopentane, isohexane, etc.

Many organic compounds can form complexes with solvents in which they are reacted or from which they are precipitated or crystallized. These complexes are known as "solvates". Solvates of compounds of structural formula I are within the scope of the present invention. Many organic compounds can exist in more than one crystalline form. For example, crystalline form may vary from solvate to solvate. Thus, all crystalline forms of the compounds of structural formula I or the pharmaceutically acceptable solvates thereof are within the scope of the present invention.

The methods may be employed in a human male facing a precipitating event, whether or not the male has received a diagnosis of BPH.

The methods may further be employed in a human male who recently has faced a precipitating event, whether or not the male has received a diagnosis of BPH.

For example, if a human male has scheduled surgery or anesthesia, he may be a suitable subject for the methods of the present invention. In another example, a human male who is taking medication or drugs known to precipitate retention may also be a suitable subject for the methods of the present invention.

Alternatively, the methods of the present invention may be employed in a male subject with a prior history of acute urinary retention, whether spontaneous or acute, in order to reduce the risk of precipitated acute urinary retention in the future or to prevent a future episode of acute urinary retention.

The term "precipitating event" is defined as anesthesia or surgery; a precipitating medical event such as stroke or congestive heart failure; a medical condition such as prostatitis or urinary tract infection; or ingestion of medication or drugs known to precipitate retention, e.g., pseudoephedrine hydrochloride, cold medicine, pain medication such as narcotics or sedatives, or benadryl.

The term "precipitated acute urinary retention" is defined as an episode of acute urinary retention that is precipitated by at least one of the precipitating events, defined above.

The term "effective amount" means the amount of 5α-reductase inhibitor that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts.

The inhibitors of 5α-reductase employed in the present invention are useful as pharmacological agents for mammals, especially for humans, for the prevention of and reduction of the risk of precipitated acute urinary retention.

Generally, the daily dosage of the 5α-reductase inhibitor may be varied over a wide range from 0.01 to 500 mg per adult human per day. In a preferred embodiment, the 5α-reductase inhibitor is administered at a dose of 1.0 to 100 mg per day. In another preferred embodiment, the 5α-reductase inhibitor is administered at a dose of 0.5 to 10 mg per day. For oral administration, the compositions are preferably provided in the form of tablets containing 0.01, 0.05, 0.1, 0.5, 1.0,. 2.5, 5.0, 10.0, 15.0, 25.0, 50.0 and 100 milligrams of active ingredient for the symptomatic adjustment of the dosage to the subject to be treated. An effective amount of the drug is ordinarily supplied at a dosage level of from about 0.0002 mg/kg to about 50 mg/kg of body weight per day. The range is more particularly from about 0.001 to 7 mg/kg of body weight per day.

The dose may be administered in a single daily dose or the total daily dosage may be administered in divided doses of two, three or four times daily. Furthermore, when administered via intranasal routes, transdermal routes, by rectal suppositories, or through a continual intravenous solution, the dosage administration will, of course, be continuous rather than intermittent throughout the dosage regimen.

In the methods of the present invention, the inhibitor of 5α-reductase inhibitor may preferably be administered to the individual to avoid the risk for precipitated acute urinary retention and to reduce the risk of having such an episode in the future. Alternatively, the administration of the 5α-reductase inhibitor may be commenced before a scheduled precipitating event (such as surgery or anesthesia) to prevent the occurrence of acute urinary retention related to the event.

Formulations of the 5α-reductase inhibitors employed in the present method for medical use comprise the 5α-reductase inhibitor together with an acceptable carrier thereof. The carrier must be pharmaceutically acceptable in the sense of being compatible with the other ingredients of the formulation and not deleterious to the recipient subject of the formulation.

According to the methods of the present invention, the 5α-reductase inhibitor may be administered as the sole active agent or together with another active agent such as an antiandrogen, a GnRH analog, a GnRH antagonist or with another 5α-reductase inhibitor.

The present invention, therefor further provides a pharmaceutical formulation comprising a 5α-reductase type 2 inhibitor together with a pharmaceutically acceptable carrier thereof.

The formulations include those suitable for oral, rectal, topical or parenteral (including subcutaneous, intramuscular and intravenous administration). Preferred are those suitable for oral administration.

The formulations may be presented in a unit dosage form and may be prepared by any of the methods known in the art of pharmacy. All methods include the step of bringing the active compound in association with a carrier which constitutes one or more ingredients. In general, the formulations are prepared by uniformly and intimately bringing the active compound in association with a liquid carrier, a waxy solid carrier or a finely divided solid carrier, and then, if needed, shaping the product into desired dosage form.

According to the formulations of the present invention, the 5α-reductase inhibitor may be the sole active agent or may be present together with another active agent such as an antiandrogen, a GnRH analog, a GnRH antagonist or with another 5α-reductase inhibitor.

Formulations of the present invention suitable for oral administration may be presented as discrete units such as capsules, cachets, tablets or lozenges, each containing a predetermined amount of the active compound; as a powder or granules; or a suspension or solution in an aqueous liquid or non-aqueous liquid, e.g., a syrup, an elixir, or an emulsion.

A tablet may be made by compression or molding, optionally with one or more accessory ingredients. Compressed tablets may be prepared by compressing in a suitable machine the active compound in a free flowing form, e.g., a powder or granules, optionally mixed with accessory ingredients, e.g., binders, lubricants, inert diluents, disintegrating agents or coloring agents. Molded tablets may be made by molding in a suitable machine a mixture of the active compound, preferably in powdered form, with a suitable carrier. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

Oral liquid forms, such as syrups or suspensions in suitably flavored suspending or dispersing agents such as the synthetic and natural gums, for example, tragacanth, acacia, methyl cellulose and the like may be made by adding the active compound to the solution or suspension. Additional dispersing agents which may be employed include glycerin and the like.

Formulations for rectal administration may be presented as a suppository with a conventional carrier, i.e., a base that is nontoxic and nonirritating to mucous membranes, compatible with the 5α-reductase inhibitors, and is stable in storage and does not bind or interfere with the release of the compound. Suitable bases include: cocoa butter (theobroma oil), polyethylene glycols (such as carbowax and polyglycols), glycol-surfactant combinations, polyoxyl 40 stearate, polyoxyethylene sorbitan fatty acid esters (such as Tween, Myrj, and Arlacel), glycerinated gelatin, and hydrogenated vegetable oils. When glycerinated gelatin suppositories are used, a preservative such as methylparaben or propylparaben may be employed.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethylene-oxide polylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Formulations suitable for parenteral administration include formulations which comprise a sterile aqueous preparation of the active compound which is preferably isotonic with the blood of the recipient. Such formulations suitably comprise a solution or suspension of a compound that is isotonic with the blood of the recipient subject. Such formulations may contain distilled water, 5% dextrose in distilled water or saline and the active compound. Often it is useful to employ a pharmaceutically and pharmacologically acceptable acid addition salt of the active compound that has appropriate solubility for the solvents employed. Useful salts include the hydrochloride isothionate and methanesulfonate salts. Useful formulations also comprise concentrated solutions or solids comprising the active compound which on dilution with an appropriate solvent give a solution suitable for parenteral administration.

The compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

The following examples are not intended to be limitations on the scope of the instant invention in any way, and they should not be so construed. Furthermore, examples are not to be construed as forming the only methods and compositions that are considered as the invention. Those skilled in the art will readily understand that known variations of the conditions, processes, methods and compositions of the following preparative procedures can be used.

EXAMPLE 1
Effect of the 5α-Reductase Inhibitor Finasteride on the Risk of Precipitated Acute Urinary Retention A total of 3040 men with moderate to severe symptoms of BPH and enlarged prostates were treated with either finasteride (17β-(N-tert-butylcarbamoyl)-3-oxo-4-aza-5α-androst-1-en-3-one, 5 mg daily) or placebo in a four year double-blind, placebo-controlled study. BPH-related outcomes were assessed every 4 months. Patients on alpha blockers, antiandrogens, with a history of chronic prostatitis, recurrent urinary tract infections, or prior prostate or bladder surgery were excluded. A total of 3016 patients randomized to treatment had efficacy data and were included in the analysis of precipitated acute urinary retention; 1513 in the finasteride group and 1503 in the placebo group.

The endpoint committee, blinded to treatment group, reviewed all study-related documents related to episodes of acute urinary retention to classify the episodes as spontaneous or precipitated by other factors. All acute urinary retentions were classified by the endpoint committee as being "clearly" BPH related ("spontaneous") if there was no clear precipitating event, such as surgery within 72 hours, a precipitating medical event (e.g. stroke), or ingestion of a medication thought to precipitate retention (e.g., pseudoephedrine hydrochloride), etc. The other episodes of acute urinary retention were classified as not "clearly" BPH related ("precipitated") since there was likely to be more than one factor (including BPH) involved that precipitated the event.

Acute urinary retention was analyzed using the log-rank test for time-to-first-event and corroborated with Fisher's exact test on the cumulative incidence.

Forty-nine (3.3%) patients in the placebo group and 23 (1.5%) patients in the finasteride group had an episode of precipitated acute urinary retention during the 4-year study period. The difference between the two groups was highly significant (p=0.002) according to both the log-rank test for time-to-event and Fisher's exact test for proportion. The finasteride versus placebo relative risk (hazard ratio) was 0.48, indicating that, compared with placebo, finasteride reduced the risk of having an episode of precipitated acute urinary retention by 52% over the 4-year study period.

EXAMPLE 2
Preparation of Human Prostatic and Scalp 5α-Reductases

Samples of human tissue were pulverized using a freezer mill and homogenized in 40 mM potassium phosphate, pH 6.5, 5 mM magnesium sulfate, 25 mM potassium chloride, 1 mM phenylmethylsulfonyl fluoride, 1 mM dithiothreitol (DTT) containing 0.25 M sucrose using a Potter-Elvehjem homogenizer. A crude nuclear pellet was prepared by centrifugation of the homogenate at 1,500×g for 15 min. The crude nuclear pellet was washed two times and resuspended in two volumes of buffer. Glycerol was added to the resuspended pellet to a final concentration of 20%. The enzyme suspension was frozen in aliquots at −80° C. The prostatic and scalp reductases were stable for at least 4 months when stored under these conditions.

EXAMPLE 3
5α-Reductase Assay

The reaction mixture for the type 1 5α-reductase contained 40 mM potassium phosphate, pH 6.5, 5 mM [7-$^3$H]-testosterone, 1 mM dithiothreitol and 500 μM NADPH in a final volume of 100 μL. The reaction mixture for the type 2 5α-reductase contained 40 mM sodium citrate, pH 5.5, 0.3 mM [7-$^3$H]-testosterone, 1 mM dithiothreitol and 500 μM NADPH in a final volume of 100 μL. Typically, the assay was initiated by the addition of 50–100 μg prostatic homogenate or 75–200 μg scalp homogenate and incubated at 37° C. After 10–50 min the reaction was quenched by extraction with 250 μL of a mixture of 70% cyclohexane: 30% ethyl acetate containing 10 μg each DHT and T. The aqueous and organic layers were separated by centrifugation at 14,000 rpm in an Eppendorf microfuge. The organic layer was subjected to normal phase HPLC (10 cm Whatman Partisil 5 silica column equilibrated in 1 ml/min 70% cyclohexane: 30% ethyl acetate; retention times: DHT, 6.8–7.2 min; androstanediol, 7.6–8.0 min; T, 9.1–9.7 min). The HPLC system consisted of a Waters Model 680 Gradient System equipped with a Hitachi Model 655α Autosampler, Applied Biosystems Model 757 variable UV detector, and a Radiomatic Model A120 radioactivity analyzer. The conversion of T to DHT was monitored using the radioactivity flow detector by mixing the HPLC effluent with one volume of Flo Scint 1 (Radiomatic). Under the conditions described, the production of DHT was linear for at least 25 min. The only steroids observed with the human prostate and scalp preparations were T, DHT and androstanediol.

Inhibition Studies

Compounds were dissolved in 100% ethanol. The compound to be tested was pre-incubated with the enzyme (either 5α-reductase type 1 or 2) prior to initiation by addition of substrate testosterone. $IC_{50}$ values represent the concentration of inhibitor required to decrease enzyme conversion of testosterone to dihydrotestosterone by 50% of the control. $IC_{50}$ values were determined using a 6 point titration where the concentration of the inhibitor was varied from 0.1 to 1000 nM. Representative compounds of this invention were tested in the above described assay for 5α-reductase type 1 and type 2 inhibition.

A compound referred to herein as a 5α-reductase 2 inhibitor is a compound that shows inhibition of the 5α-reductase 2 isozyme in the above-described assay, having an $IC_{50}$ value of about or under 100 nM.

The compounds are tested in the above-described assay for 5α-reductase type 1 and type 2 inhibition, and were found to have $IC_{50}$ values under about 100 nM for inhibition of the type 1 isozyme. Compounds found to have $IC_{50}$ values of under about 50 nM for inhibition of the type 1 isozyme are called type 1 inhibitors.

The compounds called "dual inhibitors" were inhibitors of both 5α-reductase type 1 and 5α-reductase type 2 as defined above.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the subject being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A method for reducing the risk of precipitated acute urinary retention in a male subject at risk therefor, comprising administration of an effective amount of an inhibitor of 5α-reductase to the subject.

2. A method for reducing the risk of precipitated acute urinary retention in a male subject at risk therefor, comprising administration of a compound of structural formula I to the subject:

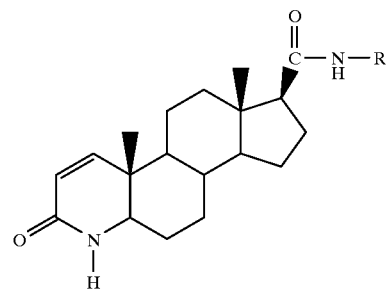

wherein R is selected from:

(a) $C_{1-10}$ alkyl, unsubstituted or substituted with one to three halogen substituents, and (b) phenyl, unsubstituted or substituted with one to three substituents independently selected from halogen, methyl, and trifluoromethyl;

or a pharmaceutically acceptable solvate or crystal form thereof.

3. The method of reducing the risk of precipitated acute urinary retention according to claim 2, wherein R is selected from:

(a) unsubstituted $C_{1-10}$ alkyl, and (b) phenyl unsubstituted or substituted with one or two trifluoromethyl substituents.

4. The method of reducing the risk of precipitated acute urinary retention according to claim 2, wherein R is t-butyl.

5. The method of reducing the risk of precipitated acute urinary retention according to claim 2, wherein R is 2,5-bis (trifluoromethyl)phenyl.

6. The method according to claim 1, wherein the precipitated acute urinary retention is precipitated by anesthesia or surgery; a precipitating medical event; a precipitating medical condition such as prostatitis or urinary tract infection; or ingestion of medication known to precipitate retention.

7. The method according to claim 6, wherein the precipitating medical event is selected from stroke and congestive heart failure; the precipitating medical condition is selected from prostatitis and urinary tract infection; and the medication known to precipitate retention is selected from pseudoephedrine hydrochloride, cold medicine, narcotics, sedatives, and benadryl.

8. The method according to claim 6, wherein the precipitated acute urinary retention is precipitated by anesthesia or surgery.

9. The method according to claim 1 for reducing the risk precipitated acute urinary retention in a subject at risk therefor, comprising administration of finasteride at a dose of 5 mg per day.

10. A method of preventing precipitated acute urinary retention in a male subject susceptible thereto, comprising administration of an effective amount of an inhibitor of 5α-reductase to the subject.

11. A method of preventing precipitated acute urinary retention in a male subject susceptible thereto, comprising administration of a compound of structural formula I to the subject:

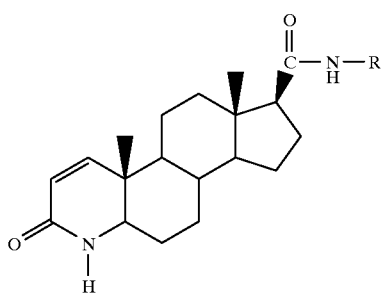

wherein R is selected from:
(a) $C_{1-10}$ alkyl, unsubstituted or substituted with one to three halogen substituents, and
(b) phenyl, unsubstituted or substituted with one to three substituents independently selected from halogen, methyl, and trifluoromethyl;
or a pharmaceutically acceptable solvate or crystal form thereof.

12. The method of preventing precipitated acute urinary retention according to claim 11, wherein R is selected from:
(a) unsubstituted $C_{1-10}$ alkyl, and
(b) phenyl unsubstituted or substituted with one or two trifluoromethyl substituents.

13. The method of preventing precipitated acute urinary retention according to claim 11, wherein R is t-butyl.

14. The method of preventing precipitated acute urinary retention according to claim 11, wherein R is 2,5-bis (trifluoromethyl)phenyl.

15. The method according to claim 10, wherein the precipitated acute urinary retention is precipitated by anesthesia or surgery; a precipitating medical event; a precipitating medical condition; or ingestion of medication known to precipitate retention.

16. The method according to claim 15, wherein the precipitating medical event is selected from stroke and congestive heart failure; the precipitating medical condition is selected from prostatitis and urinary tract infection; and the medication known to precipitate retention is selected from pseudoephedrine hydrochloride, cold medicine, narcotics, sedatives, and benadryl.

17. The method according to claim 15, wherein the precipitated acute urinary retention is precipitated by anesthesia.

18. The method according to claim 10 preventing precipitated acute urinary retention in a subject susceptible thereto, comprising administration of finasteride at a dose of 5 mg per day.

* * * * *